United States Patent
Fishman

(10) Patent No.: US 11,642,549 B2
(45) Date of Patent: May 9, 2023

(54) BEAM HARDENING FOR INTRAOPERATIVE RADIATION THERAPY USING A BALLOON APPLICATOR

(71) Applicant: EMPYREAN MEDICAL SYSTEMS, INC., Boca Raton, FL (US)

(72) Inventor: Kalman Fishman, Boca Raton, FL (US)

(73) Assignee: EMPYREAN MEDICAL SYSTEMS, INC., Boca Raton, FL (US)

( * ) Notice: Subject to any disclaimer, the term of this patent is extended or adjusted under 35 U.S.C. 154(b) by 750 days.

(21) Appl. No.: 16/742,173

(22) Filed: Jan. 14, 2020

(65) Prior Publication Data

US 2020/0222719 A1 Jul. 16, 2020

Related U.S. Application Data

(60) Provisional application No. 62/792,479, filed on Jan. 15, 2019.

(51) Int. Cl.
*A61N 5/10* (2006.01)

(52) U.S. Cl.
CPC ......... *A61N 5/1002* (2013.01); *A61N 5/1014* (2013.01); *A61N 5/1065* (2013.01); *A61N 5/1083* (2013.01); *A61N 2005/1003* (2013.01); *A61N 2005/1004* (2013.01); *A61N 2005/1089* (2013.01)

(58) Field of Classification Search
CPC ...... A61N 5/10–1084; A61N 2005/1085–1098
See application file for complete search history.

(56) References Cited

U.S. PATENT DOCUMENTS

| | | | |
|---|---|---|---|
| 7,686,755 B2 | 3/2010 | Smith et al. | |
| 2008/0009659 A1 | 1/2008 | Smith et al. | |
| 2011/0105822 A1 | 5/2011 | Roeder | |
| 2013/0003931 A1* | 1/2013 | Funk | A61N 5/1014 378/65 |

\* cited by examiner

Primary Examiner — Thaddeus B Cox
(74) Attorney, Agent, or Firm — Fox Rothschild LLP

(57) ABSTRACT

A balloon applicator for an intraoperative radiation therapy system includes an x-ray beam shaping component for emitting x-rays in a plurality of possible directions in three dimensions. The balloon applicator includes connecting structure for connecting to the intraoperative radiation therapy system and an inflatable balloon contactor having an outer surface. The balloon applicator has a beam hardening system including a beam hardening compound disposed between the x-ray beam shaping component and the outer surface of the balloon. The beam hardening system is capable of hardening the beam in beam directions in three dimensions. An intraoperative radiation therapy system and a method for conducting intraoperative radiation therapy are also disclosed.

14 Claims, 10 Drawing Sheets

BEAM HARDENING FOR INTRAOPERATIVE RADIATION THERAPY USING A BALLOON APPLICATOR

CROSS-REFERENCE TO RELATED APPLICATIONS

This application claims priority to U.S. Provisional Patent Application No. 62/792,479 filed on Jan. 15, 2019, entitled "BEAM HARDENING FOR INTRAOPERATIVE RADIATION THERAPY USING A BALLOON APPLICATOR", the entire disclosure of which is incorporated herein by reference.

FIELD OF THE INVENTION

This invention relates to radiation therapy, and more particularly to intraoperative radiation therapy.

BACKGROUND OF THE INVENTION

X-rays are widely used in the medical field for various purposes, such as radiotherapy. Radiotherapy techniques can involve an externally delivered radiation dose using a technique known as external beam radiotherapy (EBRT). Intraoperative radiotherapy (IORT) is also sometimes used. IORT involves the application of therapeutic levels of radiation to a tumor bed or other target while the area is exposed and accessible during excision surgery. The benefit of IORT is that it allows a high dose of radiation to be delivered precisely to the targeted area, at a desired tissue depth, with minimal exposure to surrounding healthy tissue. The wavelengths of X-ray radiation most commonly used for IORT purposes correspond to a type of X-ray radiation that is sometimes referred to as fluorescent X-rays, characteristic X-rays, or Bremsstrahlung X-rays. Miniature X-ray sources have the potential to be effective for IORT. A challenge with miniature X-ray sources for IORT is that the source is most desirably at least partially positioned within the body of the patient during the IORT procedure, and accordingly portions of the X-ray source assembly come in contact with the patient and must be consumable or capable of re-sterilization.

Beam hardening is the process of exposing an x-ray beam comprised of polychromatic energies through an object to achieve selective attenuation of lower energy photons. Beam hardening is accomplished by positioning a beam hardening compound, for example a metal filter, in the path of the x-ray beam between the source and the target. Beam hardening helps to reduce certain artifacts such as streaking artifacts and cupping artifacts which result from polychromatic x-rays being attenuated by the target and surrounding tissues at different rates. Beam hardening is particularly challenging in the context of IORT where equipment dimensions must be minimized and some equipment must be changed after each use due to compromised sterility.

SUMMARY OF THE INVENTION

A balloon applicator for an intraoperative radiation therapy system comprising an x-ray beam shaping component for emitting x-rays in a plurality of possible directions in three dimensions. The balloon applicator can include an inflatable balloon contactor having an outer surface, and a beam hardening system comprising a beam hardening compound disposed between the x-ray beam shaping component and the outer surface of the balloon. The beam hardening system is capable of hardening the beam in beam directions in three dimensions.

The beam hardening system can include a beam hardening compound. The beam hardening compound can be provided in an inflation fluid for inflating the balloon contactor. The balloon contactor can include a balloon wall and the beam hardening system can include a beam hardening layer on an inner surface of the balloon wall. The beam hardening layer can include a beam hardening compound. The balloon contactor can include a balloon wall and the beam hardening system can include a beam hardening layer on an outer surface of the balloon wall. The balloon contactor can include a balloon wall and the beam hardening system can include a beam hardening compound within the balloon wall.

The beam hardening system can include a beam hardening cup positioned between the x-ray beam shaping component and the wall of the balloon contactor. The beam hardening compound can be at least one selected from the group consisting of aluminum, copper and iron. The beam hardening system can be capable of providing beam hardening at any beam direction over three quarters of a sphere.

An intraoperative radiation therapy system can include a robotic system for intraoperative radiation therapy comprising a robotic arm secured at a first end to a base. A treatment head can be disposed on a second end of the robotic arm distal to the base. The treatment head can include at least one x-ray component configured to facilitate generation of therapeutic radiation in the x-ray wavelength range and at least one x-ray beam shaping component for emitting x-rays in a direction selected from a plurality of possible directions in three dimensions. A balloon applicator having an inflatable balloon contactor can be disposed to enclose at least a distal end of the treatment head from which the therapeutic radiation emanates. Fluid utility channels can be configured to communicate a fluid to and from the interior of the balloon contactor. The balloon contactor can have an outer surface for contacting patient tissue. The balloon applicator can include a beam hardening system comprising a beam hardening compound disposed between the x-ray beam shaping component and the outer surface of the balloon contactor. The beam hardening system can be capable of hardening the beam in beam directions in three dimensions. The beam hardening system is capable of providing beam hardening at any beam direction over three quarters of a sphere.

A method for conducting intraoperative radiation therapy can include the step of providing an intraoperative radiation therapy system comprising a robotic system for intraoperative radiation therapy comprising a robotic arm secured at a first end to a base and a treatment head disposed on a second end of the robotic arm distal to the base, the treatment head comprising at least one x-ray component configured to facilitate generation of therapeutic radiation in the x-ray wavelength range and at least one x-ray beam shaping component for emitting x-rays in a direction selected from a plurality of possible directions in three dimensions. The method can further include the step of providing a balloon applicator for an intraoperative radiation therapy system, the balloon applicator comprising an inflatable balloon contactor having a balloon contactor wall with an outer surface. The balloon applicator further comprises a beam hardening system comprising a beam hardening compound disposed between the x-ray beam shaping component and the outer surface of the balloon contactor wall, the beam hardening system being capable of hardening the beam in beam directions in three dimensions. The method then generates and directs an x-ray beam from the x-ray beam shaping component, and hardens the beam with the beam shaping component.

The balloon contactor and the beam hardening compound can be positioned at least in part within the body of the patient. The balloon contactor and the beam hardening compound can be positioned completely within the body of the patient.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
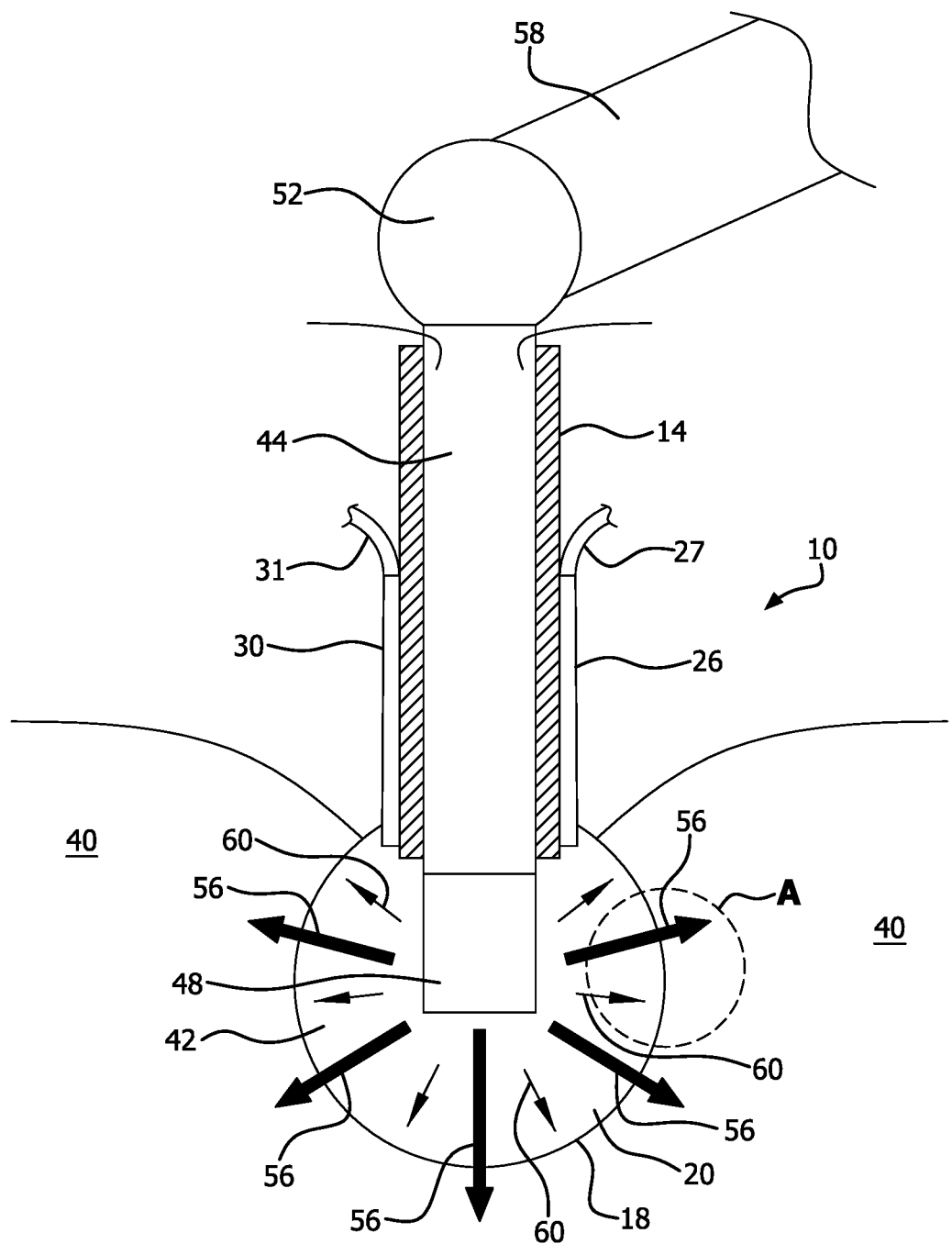
FIG. 1 is a schematic cross-sectional diagram of a balloon applicator according to the invention attached to an IORT treatment head.

A balloon applicator is provided for an intraoperative radiation therapy system which includes an x-ray beam shaping component for emitting x-rays in a direction selected from a plurality of possible directions in three dimensions. The balloon applicator includes an inflatable balloon contactor having an outer surface. The balloon applicator can also include connecting structure for connecting to the intraoperative radiation therapy system. The balloon applicator has a beam hardening system which includes a beam hardening compound disposed between the x-ray beam shaping component and the outer surface of the balloon. The beam hardening system is capable of hardening the beam in beam directions encompassing three dimensions.

A number of different constructions are possible to position the beam hardening compound between the x-ray beam shaping component and the balloon contactor. The beam hardening compound can be provided in an inflation fluid for inflating the balloon contactor and performing beam hardening. The balloon contactor can include a balloon wall, and the beam hardening system can include a beam hardening layer on an inner surface of the balloon wall. The beam hardening inner layer includes the beam hardening compound. The balloon contactor can include a balloon wall, and the beam hardening system can include a beam hardening layer which includes the beam hardening compound on an outer surface of the balloon wall. The beam hardening compound can be provided within the balloon wall.

The beam hardening system can include structures which positions a beam hardening structure between the x-ray beam shaping component and the balloon contactor. The beam hardening structure can be any such structure, for example a beam hardening cup positioned between the x-ray beam shaping component and the wall of the balloon contactor.

The beam hardening compound can be any suitable compound. Selection of the beam hardening compound will sometimes depend on the particular intraoperative radiation therapy that is planned. The invention permits changes to the beam hardening compound by interchanging the balloon applicator. The balloon applicator is removable and interchangeable, and by providing different balloon applicators with different beam hardening compounds or locations or concentrations of beam hardening compounds the beam hardening characteristics can be varied.

The beam hardening compound can be selected from many different beam hardening compounds. Common beam hardening filter materials are aluminum (Al), copper (Cu) and iron (Fe). Other materials, combinations of materials, and beam hardening alloys are possible.

Using suitable controls IORT permits for the control of a beam in three dimensions. The balloon applicator of the invention provides a beam hardening system that can be capable of providing beam hardening at different locations selected from the x, y and z axes. For example, the invention can be capable of performing beam hardening any beam direction in three dimensions, for example over three quarters of a sphere.

An intraoperative radiation therapy system includes a robotic system for intraoperative radiation therapy including a robotic arm secured at a first end to a base. A treatment head can be disposed on a second end of the robotic arm distal to the base. The treatment head includes at least one x-ray beam shaping component for emitting x-rays in a direction selected from a plurality of possible directions in three dimensions. A balloon applicator includes an inflatable balloon contactor disposed to enclose at least a distal end of the treatment head from which the therapeutic radiation emanates. Fluid utility channels are configured to communicate a fluid to and from the interior of the balloon contactor. The inflating fluid can be a liquid or a gas. The balloon contactor has an outer surface for contacting patient tissue. The balloon applicator includes a beam hardening system comprising a beam hardening compound disposed between the x-ray beam shaping component and the outer surface of the balloon contactor. The beam hardening system can be capable of hardening the beam in beam directions in three dimensions. The beam hardening system can be capable of providing beam hardening at many beam directions in the x, y and z axes, for example over three quarters of a sphere.

A method for conducting intraoperative radiation therapy can include the steps of providing an intraoperative radiation therapy system comprising a robotic system for intraoperative radiation therapy. The robotic system can include a robotic arm secured at a first end to a base and a treatment head disposed on a second end of the robotic arm distal to the base. The treatment head can include at least one x-ray beam shaping component for emitting x-rays in a direction selected from a plurality of possible directions in three dimensions. A balloon applicator can include an inflatable balloon contactor having a balloon contactor wall with an outer surface. The balloon applicator further includes a beam hardening system comprising a beam hardening compound disposed between the x-ray beam shaping component and the outer surface of the balloon contactor wall. The beam hardening system can be capable of hardening the beam in beam directions encompassing three dimensions. The method includes generating and directing an x-ray beam from the x-ray beam shaping component, and hardening the beam with the beam shaping component.

The balloon contactor and the beam hardening compound are positioned at least in part within the body of the patient. The balloon contactor and the beam hardening compound can be positioned completely within the body of the patient. The method can include removing a balloon applicator after each use and replacing with a sterile balloon applicator. The method can include determining a necessary beam hardening, and selecting a balloon applicator with an appropriate beam hardening system for the application.

The x-ray beam shaping component can be any such component for emitting x-rays in a plurality of possible directions in three dimensions. Preferably, the beam shaping component can selectively emit x-rays in any of a plurality of possible directions in three dimensions, while selectively excluding emissions in some directions. One such system is shown in US 2018/0286623 dated Oct. 4, 2018 "THREE-DIMENSIONAL BEAM FORMING X-RAY SOURCE", the disclosure of which is incorporated fully herein by reference. The intraoperative radiation therapy system can be any of several possible designs. One such system is shown in US 2018/0015303 dated Jan. 18, 2018 "ROBOTIC INTRAOPERATIVE RADIATION THERAPY" the disclosure of which is incorporated fully herein by reference.

FIG. 1 is a schematic cross-sectional diagram of a balloon applicator 10 according to the invention attached to an IORT treatment head. The balloon applicator can include an applicator cannula 14 and a balloon contactor 18. The applicator cannula 14 is used to engage an x-ray treatment head 44. The balloon contactor 18 is inflated when placed within the body 40 of the patient to contact tissue adjacent to the surgical opening as shown.

Balloon contactor 18 is flexible and can be constructed from an elastic or expandable material. The balloon contactor 18 when inflated with a fluid defines an interior space 20. The balloon contactor 18 is inflated by the addition of a fluid through suitable inflation and deflation structure. The fluid can be added as by a fluid supply channel 26 which can communicate with a fluid supply conduit 27. The fluid can be withdrawn by means of a fluid exhaust channel 30 communicating with a fluid exhaust conduit 31.

The x-ray treatment head 44 can include electron beam shaping components. The electron beam is controlled to strike a suitable target at the x-ray beam shaping component 48. The interaction between the electron beam and the x-ray beam shaping component 48 can be controlled to direct the x-ray beam emanating from the x-ray beam shaping component 48 in three dimensions. The x-ray beam emanating from the x-ray beam shaping component 48 will be polyenergetic with photons of differing velocities. This is illustrated schematically by large arrows 56 illustrating high energy photons and small arrows 60 illustrating lower energy photons.

The balloon applicator 10 can be connected to the treatment head 44 by cannula 14 which has an open interior that is dimensioned to receive the treatment head 44. The treatment head 44 can communicate with robotic arm 58 about pivot 52 which can be robotically controlled to provide precise positioning of the treatment head 44, x-ray beam shaping component 48 and balloon contactor 18.

Figure 2:
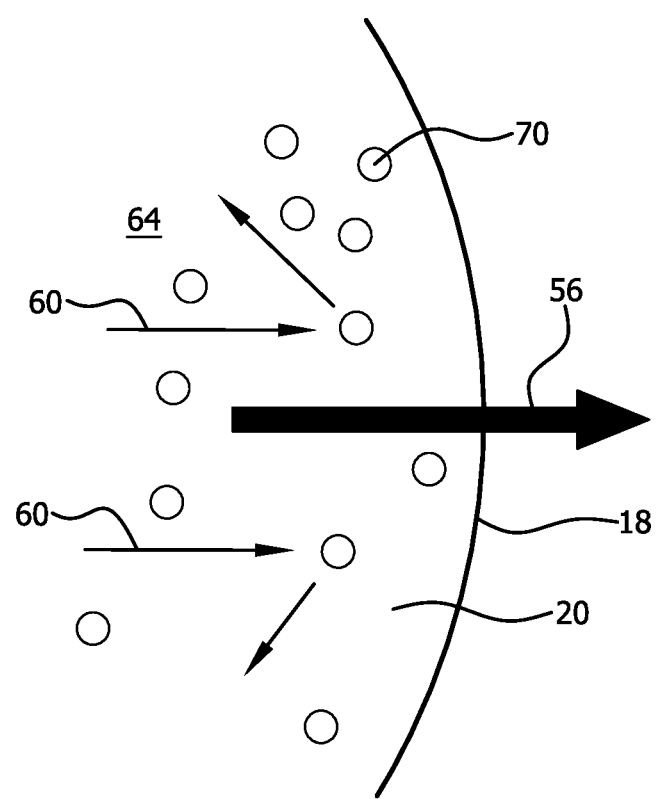
FIG. 2 is an expanded schematic diagram of area A in FIG. 1 with a first embodiment of a beam hardening system.

FIG. 2 is an expanded schematic diagram of area A in FIG. 1 with a first embodiment of a beam hardening system. In this embodiment the interior space 20 of the balloon contactor 18 is filled with fluid 64. Within the fluid 64 are particles 70 of a beam hardening compound, which can be suspended particles. High energy photons 56 pass through the fluid 64 containing the beam hardening compound 70, while low energy photons 60 are attenuated as shown. The beam hardening compound 70 and fluid 64 can be selected such that particles of the beam hardening compound 70 will remain suspended in the fluid 64 for the duration of the procedure. This can be accomplished by suitable techniques such as the selection of appropriate and compatible materials for the fluid 64 and for the beam hardening compound 70, selection of the size and density of particles forming the suspended beam hardening compound 70, and by the addition of one or more suspending agents or surfactants.

Figure 3:
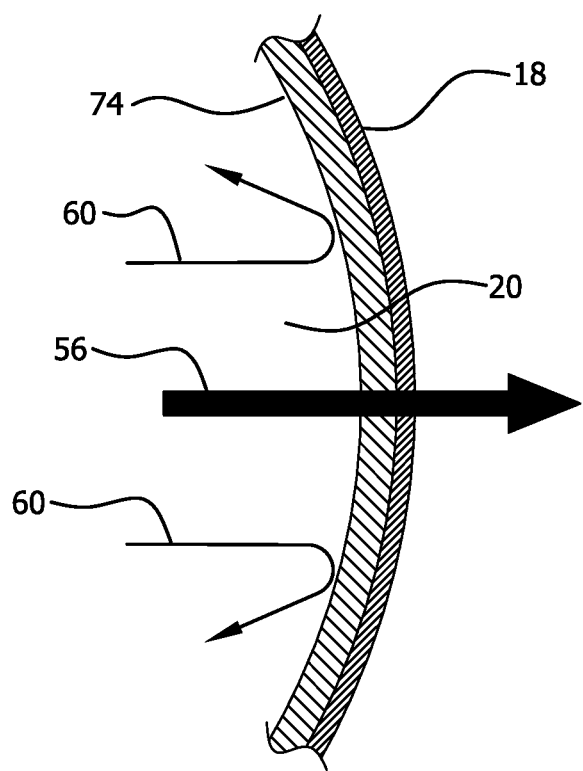
FIG. 3 is an expanded schematic diagram of area A in FIG. 1 with a second embodiment of a beam hardening system.

FIG. 3 is an expanded schematic diagram of area A in FIG. 1 with a second embodiment of a beam hardening system where the inner surface of the balloon contactor 18 is coated with an inner layer 74 of beam hardening compound or a material containing a beam hardening compound. The beam hardening layer 74 can in one embodiment be a metallic film deposited by techniques such as vapor deposition on the inner surface of the balloon contactor 18. Also, the beam hardening layer 74 can be another material in which particles or a layer of a beam hardening compound are contained. The beam hardening inner layer 74 can be adhered or otherwise secured to an inner surface of the balloon contactor 18 by suitable techniques such as adhesives. High energy photons 56 pass through the beam hardening inner layer 74 while lower energy photons 60 are attenuated as shown.

Figure 4:
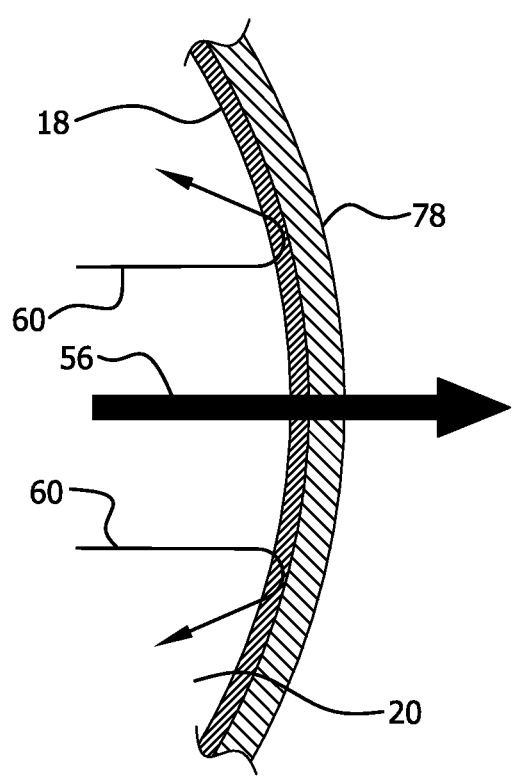
FIG. 4 is an expanded schematic diagram of area A in FIG. 1 with a third embodiment of a beam hardening system.

FIG. 4 is an expanded schematic diagram of area A in FIG. 1 with a third embodiment of a beam hardening system where the outer surface of the balloon contactor 18 is coated with an outer layer 78 of beam hard compound or material containing a beam hardening compound. The outer beam hardening layer 78 can be a metallic film deposited by techniques such as vapor deposition on the outer surface of the balloon contactor 18. The outer beam hardening layer 78 can be another material in which particles or a layer of a beam hardening compound is contained. The outer beam hardening layer 78 can be secured or adhered to an outer surface of the balloon contactor 18 by suitable techniques such as adhesives. High energy photons 56 pass through the beam hardening outer layer 78 while lower energy photons 60 are attenuated as shown.

Figure 5:
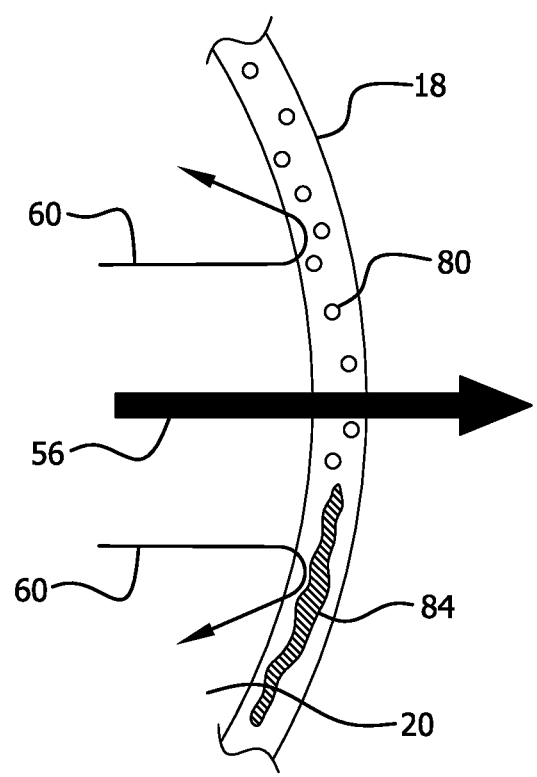
FIG. 5 is an expanded schematic diagram of area A in FIG. 1 with a fourth embodiment of a beam hardening system.

FIG. 5 is an expanded schematic diagram of area A in FIG. 1 with a fourth embodiment of a beam hardening system where the beam hardening compound 84 is provided within the balloon contactor 18. The beam hardening compound can be provided as particles 80 or a layer 84 of beam hardening compound embedded within another material forming the balloon contactor 18.

Figure 6:
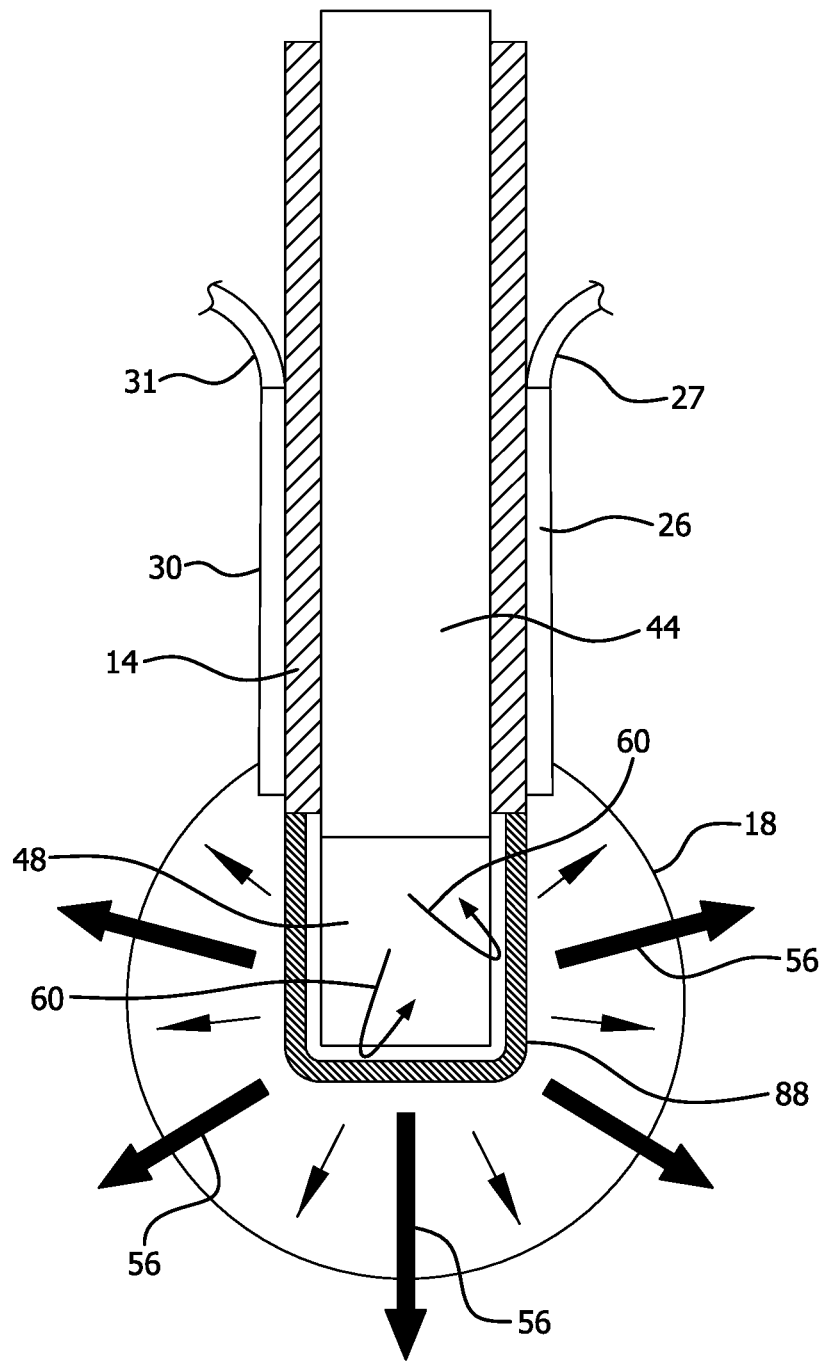
FIG. 6 is a schematic cross-sectional diagram of a balloon applicator according to the invention and having a fifth embodiment of a beam hardening system.

FIG. 6 is a schematic cross-sectional diagram of a balloon applicator according to the invention having a fifth embodiment of the beam hardening system. A filter containing a beam hardening compound is positioned at a location between the x-ray beam shaping component 48 and the balloon contactor 18. In the embodiment shown, a cup-shaped filter 88 is provided and attached to a distal end of the cannula 14 such that when the treatment head 44 and the x-ray beam shaping component 48 are positioned in the cannula 14 the beam shaping component 48 is positioned within the beam hardening cup 88. In this manner, polyenergetic x-rays emanating from the beam shaping component 48 encounter beam hardening compound in the beam hardening cup 88. Higher energy photons 56 will be able to pass the beam hardening cup 88 and the balloon contactor 18, while lower energy photons 60 will be attenuated as shown.

Figure 7:
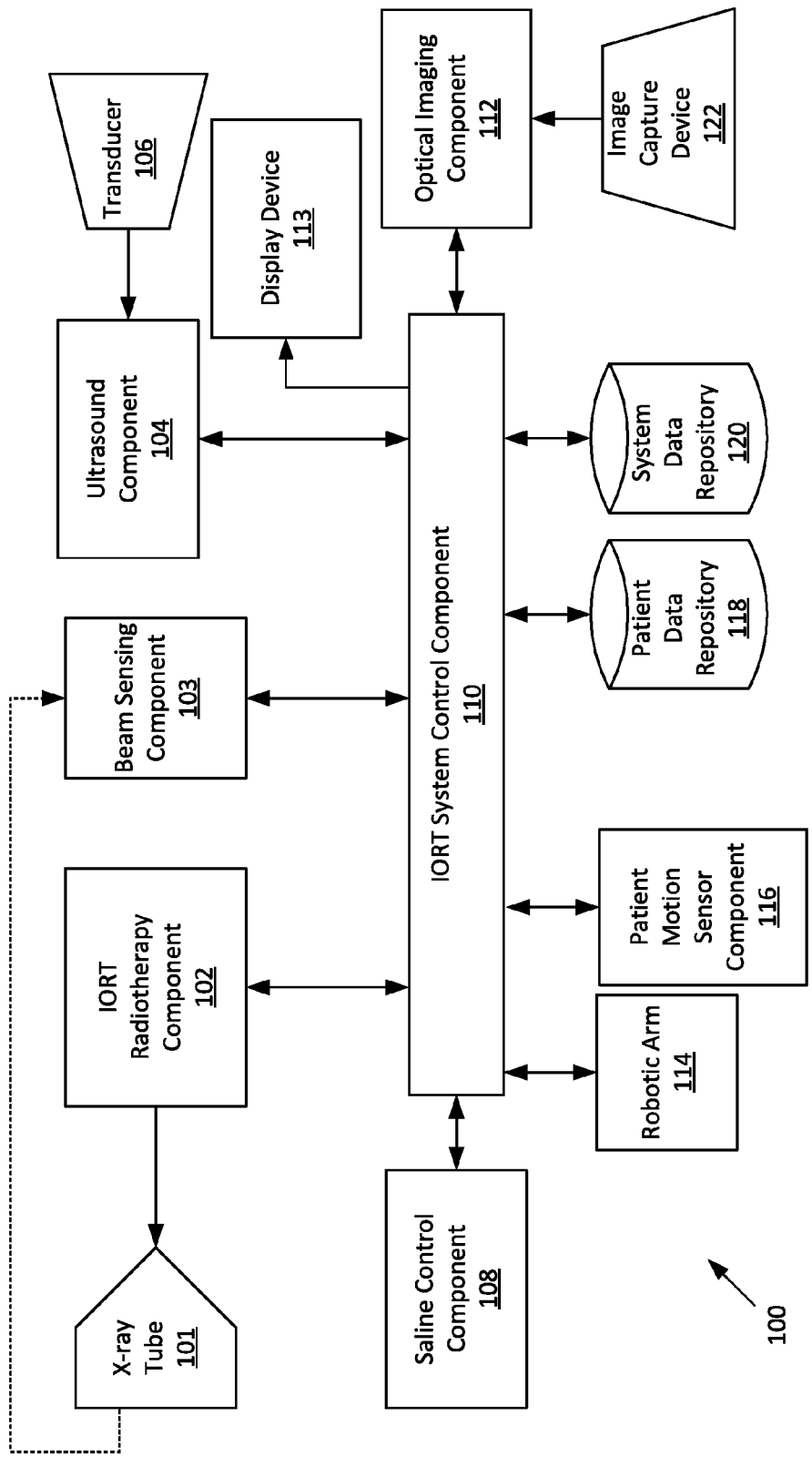
FIG. 7 is a block diagram illustrating the operation of a robotic IORT system.

FIG. 7 is a block diagram illustrating an example of the operation of a robotic IORT system. The robotic IORT system 100 can include a radiotherapy component 102 with x-ray tube 101, an optional ultrasound component 104 with a transducer 106, and an optical imaging (01) component 112 with an associated image capture device (ICD) 122. The system can include a robotic arm 114, patient motion sensor 116, and a inflating fluid control component 108. The system control component 110 guides the robotic arm 114 during IORT operations based on images and data obtained from one or more patient motion sensor components 116, the ultrasound component 104, transducer 106, the 01 component 112, and ICD 122. A display device 113, patient data repository 118, and system data repository 120 also can be provided.

An x-ray beam sensing component 103 can monitor beam output from the radiotherapy component and 102 and x-ray tube 101 along with overall system stability and yield. The x-ray beam sensing component 103 can indirectly monitor the performance of the beam hardening system by determining the characteristics of the x-ray beam that is emanating from the x-ray beam shaping component and thereby the characteristics of beam hardening and the beam hardening compound that will be necessary for the procedure.

When IORT operations are to be performed, the balloon applicator and the treatment head are positioned in the body cavity and the balloon applicator is inflated with fluid. Once inflated, the x-ray tube 101 and radiotherapy component 102 are used to apply radiation to the walls of the cavity formed in the patient. During the application of radiation, the inflating fluid control component can monitor them and maintain fluid circulation and can pressure within the balloon. After IORT treatment has been completed, the inflating fluid control component 108 releases the inflating fluid to deflate the balloon in the balloon can be withdrawn from the cavity.

Figure 8:
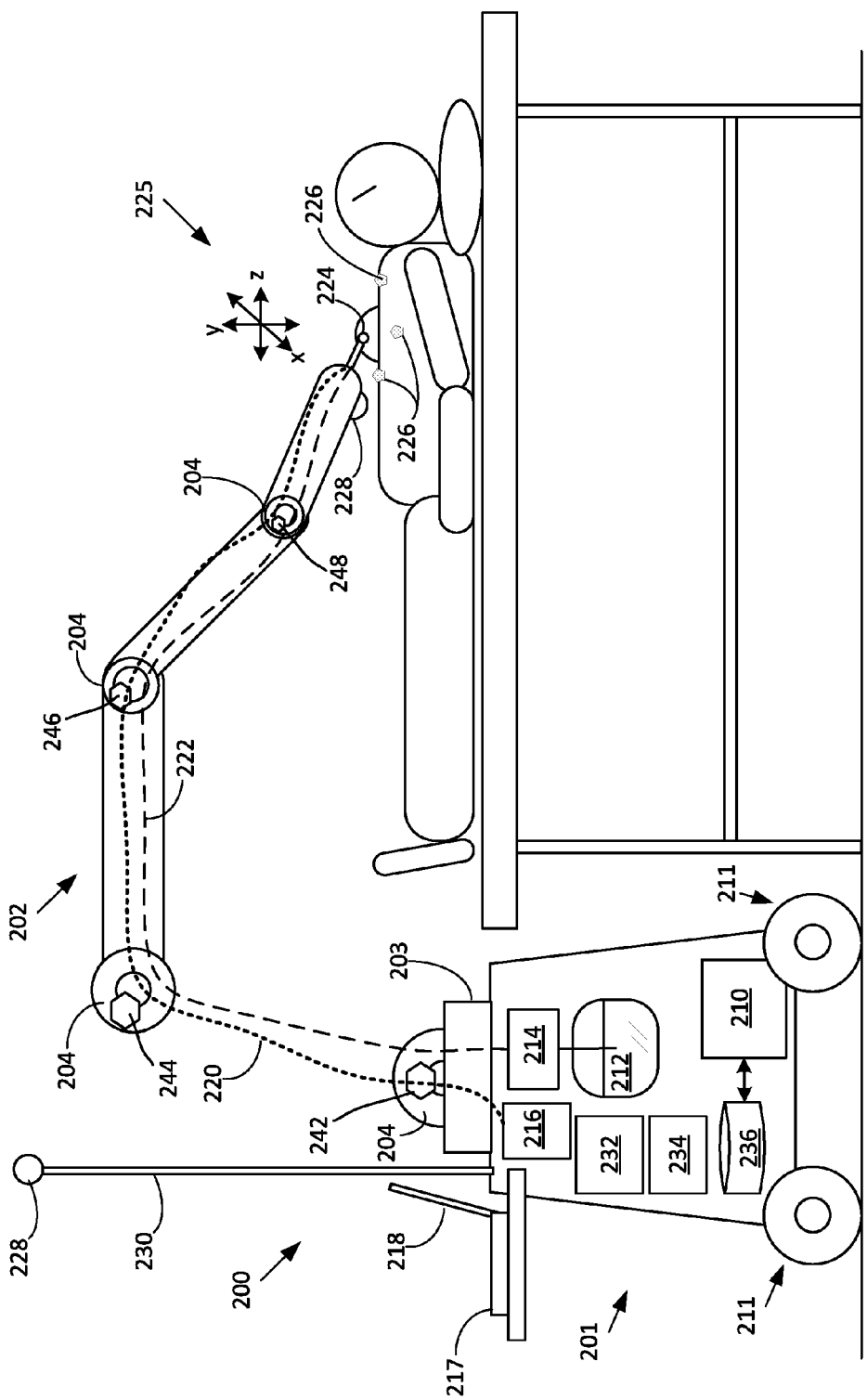
FIG. 8 is a schematic illustration of an implementation of a robotic IORT using a robotic arm to maneuver the treatment head.

FIG. 8 is a schematic illustration of an implementation of a robotic IORT using a robotic arm in the treatment head. The robotic IORT system 200 can include a base unit 201 and a robotic arm 202, radiotherapy treatment device 216, inflating fluid reservoir 212, an inflating fluid control element 214, and a system control component 210. The base unit 201 can be mounted on wheels 211 to provide mobility. The base unit can also include an optical imaging component 232, an ultrasound component 234, and a data storage device 236 for storing patient and/or system data. The base unit 201 can include a power lead for optionally providing power to all the components housed in or connected to the base unit 201. The base unit 201 can contain one or more computers 217 for controlling the system 200 and/or analyzing and processing data obtained from the system 200 components. A monitor 218 can also be mounted to the base unit 201 for user interface. A terminal or an input device such as a keyboard or mouse can also be included. Fiducial markers 226 can be provided and monitored by sensors 228 and optionally sensing support structure 230 can be provided.

A mount 203 is provided on the base unit 201 for mounting the robotic arm 202. The robotic arm 202 can include a treatment head 224 which can include removable and replaceable balloon applicators of the invention for beam hardening the applied IORT. The robotic arm 202 is articulated with appropriate robotic joints or articulation members 204 under the control of the system control component 210. Additional articulations can also be provided different points of robotic arm 202 to increase the number of degrees of freedom 225 of placing, orienting and moving treatment head 224. An inflating fluid conduit 222 can facilitate communication of inflating fluid from the reservoir 212 and inflating fluid control component 214 to the treatment head 224. Power and/or control signals can be communicated from the radiotherapy treatment device 216 to the treatment head 224 by control line 220 to control and facilitate operation of the X-ray tube. The force of patient tissue movement exerted on the treatment head can be sensed by physical sensors 242, 244, 246, and 248 located in any of several positioned throughout the robotic arm 202.

Figure 9:
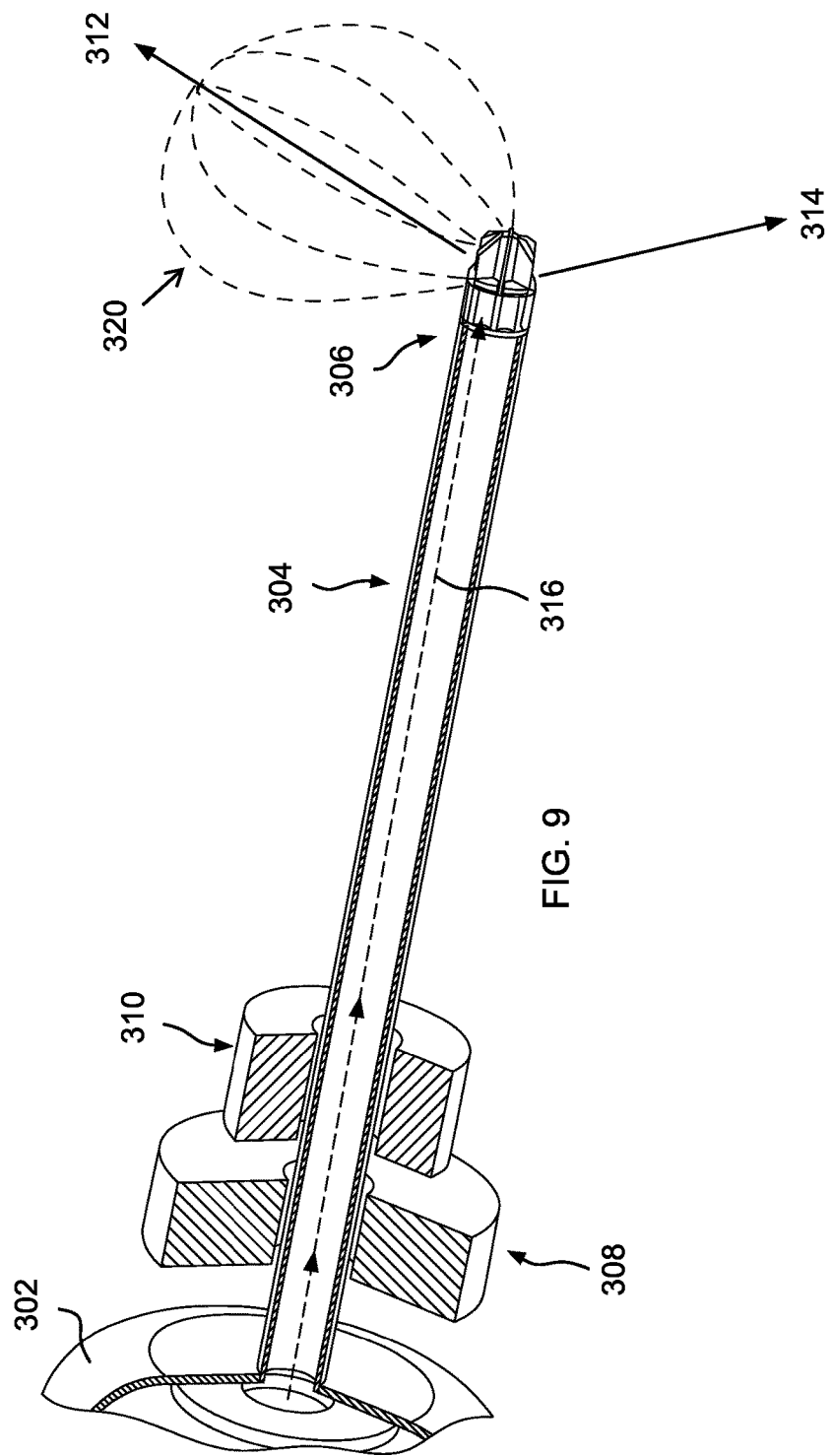
FIG. 9 is a schematic diagram illustrating an x-ray beam shaping operation in an IORT x-ray source.

FIG. 9 is a schematic diagram illustrating an x-ray beam shaping operation in an IORT x-ray source that is capable of emitting x-ray beams in three dimensions. The treatment head 304 includes a beam directionally controlled target assembly (DCTA) 306 comprising the x-ray source, beam focusing unit 308 and a beam steering unit 310. An envelope 302 encloses a vacuum chamber. An x-ray beam can be aligned in a plurality of different directions 312, 314 by selectively controlling the electron beam 316. The exact three-dimensional shape or relative intensity pattern 320 of the x-ray beam will vary in accordance with several factors. In some scenarios, the electron beam can be rapidly steered so that different target segments are success of the successively bombarded with electron so that the electron beam intersex different target segments for predetermined dwell times. If more than one target segment is bombarded by the electron beam, then multiple beam segments can be formed in selected directions defined by the associated beam-formers and each can have a different beam shape or pattern.

Figure 10:
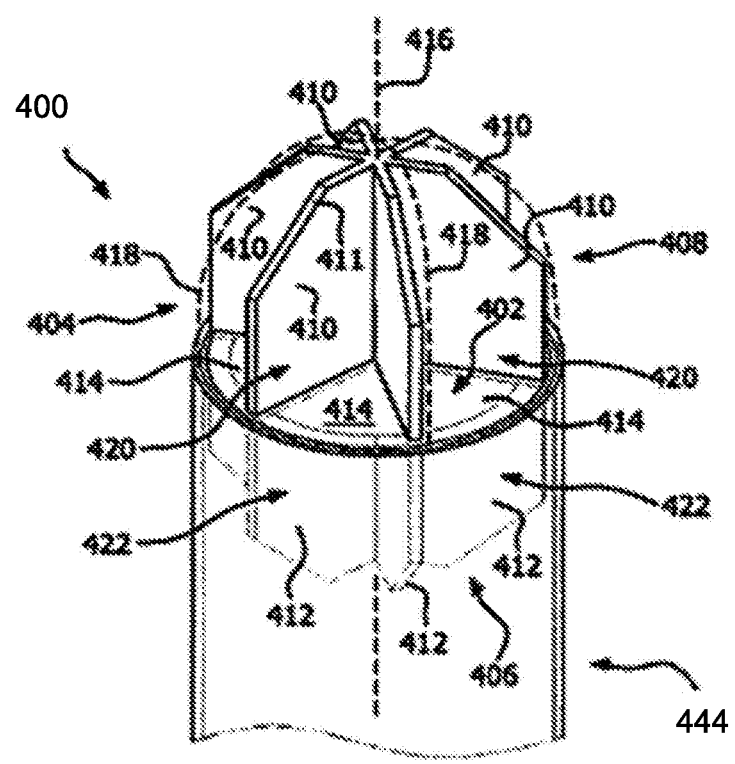
FIG. 10 is a schematic perspective view, partially in phantom, of a beam shaping component of an IORT.

FIG. 10 is a schematic perspective view, partially in phantom, of a directionally controlled target assembly (DCTA) or beam shaping component for the x-ray source of an IORT 400. Other designs for a DCTA or beam shaping component are possible. The beam shaping component is comprised of a target 402 and a beam shield 404. The target 402 is comprised of a disk-shaped element, which is disposed transverse to the direction of electron beam travel. The beam shield 404 can include a first portion 406 which is disposed adjacent to one major surface of the target 402, and a second portion 408, which is disposed adjacent to an opposing major surface of the target. In some scenarios, the first portion 406 can be disposed internal of the drift tube 444 within a vacuum environment, and the second portion 408 can be disposed external of the drift tube. If a portion of the beam shield 404 is disposed external of the drift tube then an x-ray transmissive cap member 418 can be disposed over the second portion 408 of the beam shield to enclose and protect the portions of the DCTA external of the drift tube. The cap member is indicated by dotted lines and it should be understood that the cap member 418 would extend from the end of the drift tube 444 so as to enclose the first portion 406 of the DCTA.

The beam shield 404 is comprised of a plurality of wall elements 410, 412. The wall elements 410 associated with the first portion 406 can extend from a first major surface of the disk-shaped target which faces in a direction away from the electron beam generator. The wall shaped elements 412 associated with the second portion 408 can extend from the opposing major surface of the target facing toward the electron beam generator. The wall elements 410, 412 also extend in a radial direction outwardly from the centerline 416 toward a periphery of the disk-shaped target 402. Accordingly the wall elements form a plurality of shielded compartments 420, 422. The wall elements 410, 412 can be advantageously comprised of the material which interacts in a substantial way with x-ray photons. In some scenarios, the material can be one interacts with the x-ray photons in a way which causes the x-ray photons to give up a substantial part of its energy and momentum. Accordingly one type of suitably interactive material for this purpose can comprise material that it attenuates or absorbs x-ray energy. In some scenarios the material chosen for this purpose can be advantageously chosen to be one that is highly absorbent of X-ray energy.

Suitable materials which are highly absorptive of x-ray radiation are well known. For example, these materials can include certain metals such as stainless steel, molybdenum (Mo), tungsten (W), tantalum (Ta), or other high atomic number (high-Z) materials. As used herein the phrase high-Z material will generally include those which have an atomic number of at least 21. There may be some scenarios in which a lesser degree of x-ray absorption is desired. In such scenarios a different material may be suitable. Accordingly, a suitable material for the shield wall is not necessarily limited to high atomic number materials.

The plurality of wall elements extend radially outward from the centerline 416. However the configuration of the beam shield is not limited in this regard and it should be understood that other beam shield configurations are possible. Several of such alternative configurations are described below in further detail. Each of the wall elements can comprise rounded or chamfered corners 411 to facilitate beam formation as described below. The rounded or chamfered corners can be disposed at portions of the wall elements, which are distal from the target 402 and spaced apart from the centerline 416.

The wall elements 410 can be aligned with wall elements 412 to form aligned pairs of shielded compartments 420, 422 on opposing sides of the target 402. Each such shielded compartment will be associated with a corresponding target segment 414 which is bounded by a pair of wall elements 410 on one side of the target 402, and a pair of wall elements 412 on an opposing side of the target.

As is known, X-ray photons are released in directions which are generally transverse to the collision path of the electron-beam with the major surface of the target 402. The target material is comprised of a relatively thin layer of target material such that electrons bombarding the target 402 produce X-rays in directions extending away from both major surfaces of the target. Each aligned pair of shielded compartments 420, 422 (as defined by wall elements 410, 412) and their corresponding target segment 414 comprise a beam-former of the beam shaping component. X-rays which are generated in high-energy electrons interact with a particular target segment 414 will be limited in their direction of travel by the wall elements defining the compartments 410, 412.

An electron-beam bombards a segment of target 402 to produce transmitted and reflected x-rays in directions that are generally transverse to the collision path of the electron beam. However, the x-rays will only be transmitted over a limited range of azimuth and elevation angles $\alpha$, $\beta$ due to the shielding effect of the beam-former. By selectively controlling which target segment 414 is bombarded with electrons, and where within the target segment 414 that the electron-beam actually strikes the target segment, the x-ray beams in a range of different directions and shapes can be selectively formed and sculpted as needed.

This invention can be embodied in other forms without departing from the spirit or essential attributes thereof. Accordingly, reference should be made to the following claims to determine the scope of the invention.

I claim:

1. A balloon applicator for an intraoperative radiation therapy system comprising an x-ray beam shaping component for emitting x-rays in a plurality of possible directions in three dimensions, the balloon applicator comprising an inflatable balloon contactor having an outer surface and comprising a beam hardening system comprising a beam hardening compound disposed between the x-ray beam shaping component and the outer surface of the balloon contactor, the beam hardening system being capable of hardening the beam of the emitted x-rays in beam directions in three dimensions, wherein the balloon contactor comprises a balloon wall and the beam hardening system comprises a beam hardening layer on an inner surface of the balloon wall, the beam hardening layer comprising the beam hardening compound.

2. The balloon applicator of claim 1, wherein the beam hardening compound is at least one selected from the group consisting of aluminum, copper and iron.

3. The balloon applicator of claim 1, wherein the beam hardening system is capable of providing beam hardening at any beam direction over three quarters of a sphere.

4. An intraoperative radiation therapy system, comprising:
　　a robotic system for intraoperative radiation therapy comprising a robotic arm secured at a first end to a base;
　　a treatment head disposed on a second end of the robotic arm distal to the base;
　　the treatment head comprising at least one x-ray component configured to facilitate generation of therapeutic radiation in the x-ray wavelength range and at least one x-ray beam shaping component for emitting x-rays in a direction selected from a plurality of possible directions in three dimensions;
　　a balloon applicator having an inflatable balloon contactor with an interior and disposed to enclose at least a distal end of the treatment head from which the therapeutic radiation emanates, wherein fluid utility channels are configured to communicate a fluid to and from the interior of the balloon contactor, the balloon contactor having an outer surface for contacting patient tissue; and,
　　the balloon applicator comprising a beam hardening system comprising a beam hardening compound disposed between the at least one x-ray beam shaping component and the outer surface of the balloon contactor, the beam hardening system being capable of hardening the beam of the emitted x-rays in beam directions in three dimensions.

5. The intraoperative radiation therapy system of claim 4, wherein the beam hardening system is capable of providing beam hardening at any beam direction over three quarters of a sphere.

6. A method for conducting intraoperative radiation therapy, the method comprising the steps of:
　　providing an intraoperative radiation therapy system comprising a robotic system for intraoperative radiation therapy comprising a robotic arm secured at a first end to a base and a treatment head disposed on a second end of the robotic arm distal to the base, the treatment head comprising at least one x-ray component configured to facilitate generation of therapeutic radiation in the x-ray wavelength range and at least one x-ray beam shaping component for emitting x-rays in a direction selected from a plurality of possible directions in three dimensions;

providing a balloon applicator for the intraoperative radiation therapy system, the balloon applicator comprising an inflatable balloon contactor having a balloon contactor wall with an outer surface, the balloon applicator further comprising a beam hardening system comprising a beam hardening compound disposed between the at least one x-ray beam shaping component and the outer surface of the balloon contactor wall, the beam hardening system being capable of hardening the beam of the emitted x-rays in beam directions in three dimensions;

generating an x-ray beam from the at least one x-ray component and directing the x-ray beam with the at least one beam shaping component, and hardening the x-ray beam with the beam hardening system.

7. The method of claim 6, wherein the balloon contactor and the beam hardening compound are positioned at least in part within a body of a patient.

8. The method of claim 6, wherein the balloon contactor and the beam hardening compound are positioned completely within a body of a patient.

9. A balloon applicator for an intraoperative radiation therapy system comprising an x-ray beam shaping component for emitting x-rays in a plurality of possible directions in three dimensions, the balloon applicator comprising an inflatable balloon contactor having an outer surface and comprising a beam hardening system comprising a beam hardening compound disposed between the x-ray beam shaping component and the outer surface of the balloon, the beam hardening system being capable of hardening the beam of the emitted x-rays in beam directions in three dimensions, wherein the balloon contactor comprises a balloon wall and the beam hardening system comprises a beam hardening layer on an outer surface of the balloon wall, the beam hardening layer comprising the beam hardening compound.

10. The balloon applicator of claim 9, wherein the beam hardening compound is at least one selected from the group consisting of aluminum, copper and iron.

11. The balloon applicator of claim 9, wherein the beam hardening system is capable of providing beam hardening at any beam direction over three quarters of a sphere.

12. A balloon applicator for an intraoperative radiation therapy system comprising an x-ray beam shaping component for emitting x-rays in a plurality of possible directions in three dimensions, the balloon applicator comprising an inflatable balloon contactor having an outer surface and comprising a beam hardening system comprising a beam hardening compound disposed between the x-ray beam shaping component and the outer surface of the balloon, the beam hardening system being capable of hardening the beam of the emitted x-rays in beam directions in three dimensions, wherein the balloon contactor comprises a balloon wall and the beam hardening system comprises the beam hardening compound within the balloon wall.

13. The balloon applicator of claim 12, wherein the beam hardening compound is at least one selected from the group consisting of aluminum, copper and iron.

14. The balloon applicator of claim 12, wherein the beam hardening system is capable of providing beam hardening at any beam direction over three quarters of a sphere.

* * * * *